United States Patent [19]

Sarantakis

[11] 4,204,990
[45] May 27, 1980

[54] SOMATOSTATIN ANALOGUES

[75] Inventor: Dimitrios Sarantakis, West Chester, Pa.

[73] Assignee: American Home Products Corporation, New York, N.Y.

[21] Appl. No.: 895,577

[22] Filed: Apr. 12, 1978

Related U.S. Application Data

[63] Continuation-in-part of Ser. No. 777,276, Mar. 14, 1977, and a continuation-in-part of Ser. No. 830,929, Sep. 6, 1977, abandoned.

[51] Int. Cl.² .................... C07C 103/52; A61K 37/00
[52] U.S. Cl. .............................. 260/112.5 S; 424/177
[58] Field of Search ................................ 260/112.5 S

[56] References Cited

U.S. PATENT DOCUMENTS

| | | | |
|---|---|---|---|
| 4,061,608 | 12/1977 | Sarantakis | 260/112.5 S |
| 4,062,816 | 12/1977 | Shields | 260/112.5 S |
| 4,087,390 | 5/1978 | Shields | 260/112.5 S |
| 4,093,574 | 6/1978 | Shields | 260/112.5 S |

OTHER PUBLICATIONS

Rivier et al., J. Med. Chem. 18, 123 (1975).
Rivier et al., BBRC 65, 746 (1975).
Brown et al., Metabolism 25, No. 11, Suppl. 1, Nov. (1976).
Rivier et al., Peptides (Apr. 11-17, 1976), pp. 437-443.

*Primary Examiner*—Delbert R. Phillips

*Attorney, Agent, or Firm*—Richard K. Jackson

[57] ABSTRACT

Polypeptides of the formula:

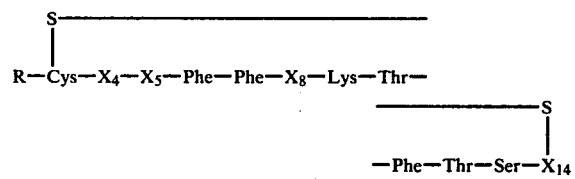

the linear precursors and non-toxic acid addition salts thereof, wherein:

R is hydrogen, lower alkanoyl, benzoyl, Ala-Gly-, Gly-Gly-Gly-, Ala-D-Ala- or p-Glu;
$X_4$ is Arg or Lys;
$X_5$ is a D-$\alpha$-amino acid;
$X_8$ is L-Trp or D-Trp; and
$X_{14}$ is Cys or D-Cys are described. These somatostatin analogues are useful as inhibitors of growth hormone and insulin secretion, selectively inhibiting growth hormone, insulin and glucagon and they demonstrate prolonged growth hormone inhibition for periods exceeding two hours. The compounds of this invention are useful in the treatment of diabetes, acromegaly and other dysfunctions characterized by excessive secretion of growth hormone and/or insulin.

7 Claims, No Drawings

SOMATOSTATIN ANALOGUES

RELATED APPLICATIONS

This application is a continuation-in-part of application Ser. No. 777,276, filed Mar. 14, 1977, and a continuation-in-part of application Ser. No. 830,929, filed Sept. 6, 1977 now abandoned.

DESCRIPTION OF THE INVENTION

In accordance with this invention, there is provided a group of polypeptides of the following formula:

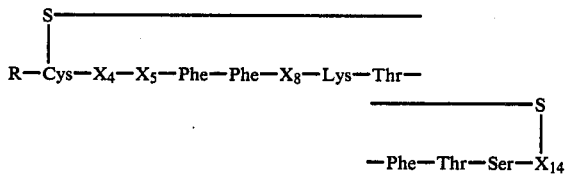

the linear precursors and non-toxic acid addition salts thereof, in which:

R is hydrogen, lower alkanoyl, benzoyl, Ala-Gly, Gly-Gly-Gly, Ala-D-Ala, or p-Glu;
$X_4$ is Arg or Lys;
$X_5$ is a D-α-amino acid;
$X_8$ is L-Trp or D-Trp; and
$X_{14}$ is Cys or D-Cys.

The specific D-amino acid representing $X_5$ in the structural formula does not appear to be critical to the activity of the compounds of this invention in that neither the overall decrease of either growth hormone, insulin or glucagon is altered by changes in the identity of that moiety nor is the prolonged decrease of growth hormone so effected. The D-α-amino acid representing $X_5$ may be D-Tyr, D-Trp, D-Phe, D-Arg, D-Lys, D-Ser, D-Ala, D-His, D-Leu, D-Met, and the like.

The preferred compounds of this invention are those of the formula:

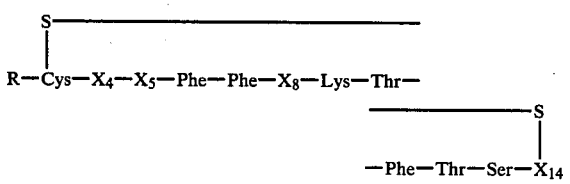

where
R is H;
$X_4$ is Arg or Lys;
$X_5$ is D-Tyr, D-Trp, D-Ser, D-His, or D-Arg,
their linear precursors or a non-toxic phramaceutically acceptable acid addition salt thereof.

These compounds inhibit the secretion of growth hormone, insulin and in some cases, glucagon, demonstrating prolonged growth hormone suppression, and like somatostatin, they are useful in the treatment of diabetes mellitus, acromegaly, and other diseases characterized by excessive secretion of growth hormone and insulin.

The polypeptides of this invention are produced by the well-known solid phase method as described by Stewart et al., Solid Phase Peptide Synthesis, Freeman and Co., San Francisco, 1969. As applied to the compounds of this invention, α-amino and sulfhydryl protected D-cysteine is attached to a chloromethylated polystyrene resin followed by removal of the α-amino protecting group with trifluoroacetic acid in methylene chloride, trifluoroacetic acid alone or HCl in dioxane. The deprotection is conducted at a temperature about 0° C. and room temperature. Other standard cleaving reagents and conditions for removal of specific α-amino protecting groups may be used as described in Schroder E. Lubke, "The Peptides", 1, 72–75 (Academic Press, 1975). After removal of the α-amino protecting group, the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Annal. Biochem., 34, 595 (1970). Where incomplete coupling has occurred, the reaction is repeated before the α-amino protecting group is removed for introduction of the next amino acid or amino acid sequence. The coupling reagents employed were N-hydroxybenzotriazole and diisopropylcarbodiimide.

After the desired amino acid sequence has been synthesized, the polypeptide is removed from the resin support by treatment with hydrogen fluoride and anisole to obtain the fully deprotected linear polypeptide. The cyclic disulfide is produced by air oxidation or with potassium ferricyamide, for example.

Non-toxic acid addition salts of the linear and cyclic polypeptides are produced by methods well known in the art from hydrochloric, hydrobromic, sulfuric, phosphoric, polyphosphoric, maleic, acetic, citric, benzoic, succinic, malonic, or ascorbic acid and the like.

The protecting groups employed throughout the solid phase synthesis are well known to the art. In selecting a particular side chain protecting group to be used in the synthesis of the peptides of this invention, the following rules should be followed: (a) the side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The following Examples illustrate the preparative technique applicable in the production of the compounds of this invention. By introducing a lower alkanoic acid, benzoic acid, Boc-Ala-Gly-OH, Boc-Gly-Gly-Gly-OH, Boc-Ala-D-Ala-OH, or p-Glu-OH into the solid phase reactor as the thirteenth amino acid moiety, there is obtain the corresponding polypeptide variables on the N-terminal $Cys^3$ group. These latter compounds exhibit the same activity as the corresponding polypeptides on which R is hydrogen.

EXAMPLE 1 tert-Butyloxycarbonyl-S-p-methoxybenzyl-L-cysteinyl-N$^g$-tosyl-L-arginyl-0-2,6-dichlorobenzyl-D-tyrosyl-L-phenylalanyl-L-phenylalanyl-D-tryptophyl-$\epsilon$-2-chlorobenzyl-oxycarbonyl-L-lysyl-0-benzyl-L-threonyl-L-phenylalanyl-0-benzyl-L-threonyl-0-benzyl-L-seryl-S-p-methoxybenzyl-D-cysteinyl-hydroxymethyl-polystyrene ester Chloromethylated polystyrene resin (Lab. Systems, Inc.) 1% cross-linked with divinylbenzene was esterified with Boc-D-Cys-(SMBzl)OH according to Gisin, Helv. Chim. Acta, 56, 1976 (1973). The polystyrene resin ester was treated according to Schedule A for the incorporation of Boc-Ser(Bzl)-OH, Boc-Thr(Bzl)-OH, Boc-Phe-OH, Boc-Thr(Bzl)-OH, Boc-Lys(ClZ)-OH, Boc-D-Trp-OH, Boc-Phe-OH, Boc-Phe-OH, Boc-D-Try(Cl$_2$Bzl)-OH, Boc-Arg(Tos)-OH and Boc-Cys(SMBzl)-OH to afford the title peptido resin.

Schedule A
1. Wash with CH$_2$Cl$_2 \times 3$;
2. Treat with TFA-CH$_2$Cl$_2$-EDT (1:1:5%, v/v) for 5 min.;
3. Treat as in 2 for 25 min;
4. Wash with CH$_2$Cl$_2 \times 3$;
5. Wash with DMF;
6. Treat with 12% TEA in DMF twice for 3 min.;
7. Wash with DMF;
8. Wash with CH$_2$Cl$_2 \times 3$;
9. Treat with 4 equivalents of the corresponding amino acid derivative in CH$_2$Cl$_2$-DMF and stir for 5 min.;
10. Add in two portions 5 equivalents of DIC dissolved in CH$_2$Cl$_2$ and over a period of 30 min.; reaction time 6 hours;
11. Wash with DMF$\times 3$;
12. Wash with CH$_2$Cl$_2 \times 3$; and
13. Test ninhydrin reaction according to Kaiser et al., Annal. Biochem, 34, 595 (1970). In case of incomplete reaction repeat lines 9 to 13 as above.

L-Cysteinyl-L-arginyl-D-tyrosyl-L-phenylalanyl-L-phenylalanyl-D-tryptophyl-L-lysyl-L-threonyl-L-phenylalanyl-L-threonyl-L-seryl-D-cysteine cyclic (1→12) disulfide The peptido resin of the previous example (16 g.) was mixed with anisole 20 ml. and treated with liquid HF (200 ml.) for 45 minutes. The excess HF was removed in vacuo and the residue was extracted with 20% aq. AcOH. The aqueous solution was extracted with ether and then the aqueous phase was neutralized with dil. NH$_4$OH to pH 7.1 and left to stand for 2 days in the open air. The mixture was acidified with gl. AcOH to pH 5 and lyophilized. The crude product was applied onto a column of Sephadex G-15 and eluted with 10% aq. AcOH. Fractions of 5.5 ml. were collected and the material which emerged between fractions 80 to 109 was collected to yield 108 mg. of the title compound.

R$_f$ (n-butanol-water-gl. AcOH, 4:5:1, v/v) 0.64.

R$_f$ (n-butanol-water-gl. AcOH-pyridine, 30:24:6:20, v/v) 0.70.

The activity of the product of the preceding preparatory example, illustrative of the other polypeptides of this invention, was determined by the following procedure:

Albino male rats were administered Nembutal intraperitoneally at a dose of 50 milligrams per kilogram. Fifteen minutes later a subcutaneous injection of the test compound or physiological saline was administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot was assayed for growth hormone, insulin and glucagon. The results of the assay are as follows:

| Compound | Dose µg/kg | GH ng/ml | INS µg/ml | GLUN pg/ml |
| --- | --- | --- | --- | --- |
| Control | — | 176 ± 33 | 340 ± 17 | 48 ± 5 |
| [des-Ala$^1$-Gly$^2$], Arg$^4$, D-Tyr$^5$, D-Trp$^8$, D-Cys$^{14}$-SRIF | 3,000 | 17 ± 3* | 48 ± 9* | 23 ± 4* |
| Control | — | NA | 43 ± 3 | 46 ± 6 |
| [des-Ala$^1$-Gly$^2$], Arg$^4$, D-Tyr$^5$, D-Trp$^8$, D-Cys$^{14}$-SRIF | 100 | NA | 7 ± 2* | 31 ± 4 |
| SRIF | 200 | NA | 31 ± 2* | 21 ± 4* |

\* = p <0.01
= p >0.05

To demonstrate prolonged activity of the compounds of this invention, [des-Ala$^1$-Gly$^2$],Arg$^4$, D-Tyr$^5$, D-Trp$^8$, D-Cys$^{14}$-somatostatin, as a representative compound of the invention, was administered (SC) to non-fasted male Charles River CD® rats with vehicle administration (SC) to control rats paired with the experimental rats. The animals were kept in separate cages. Twenty minutes before the end of the test, 50 mg/kg Nembutal® was administered to all the rats (i.p.). Blood samples were taken by cardiac puncture at 2, 4, and 6 hour intervals. Plasma was separated and growth hormone concentration was determined by radio immunoassay. Comparisons between the control and experimental growth hormone values were evaluated by the Student "t" test and statistical significance at the 0.05 level or lower was used as the index of activity. Based upon that test [Brazeau et al., Science, 170, 77 (1973)], the prolonged growth hormone suppression by the compounds of this invention was established. The data obtained for the product of Example 1, illustrative of the duration of activity of the other compounds of this invention, is as follows:

| Compound | Dose µg/kg | Time hours after injection | Plasma GH ng/ml |
| --- | --- | --- | --- |
| Control | — | 2 | 542 ± 145 |
| [des-Ala$^1$-Gly$^2$], Arg$^4$, D-Tyr$^5$, D-Trp$^8$, D-Cys$^{14}$-SRIF | 1,000 | 2 | 30 ± 5* |
| Control | — | 4 | 107 ± 25 |
| [des-Ala$^1$-Gly$^2$], Arg$^4$, D-Tyr$^5$, D-Trp$^8$, D-Cys$^{14}$-SRIF | 1,000 | 4 | 37 ± 6* |
| Control | — | 6 | 103 ± 17 |
| [des-Ala$^1$- | 500 | 6 | 152 ± 27 |

-continued

| Compound | Dose μg/kg | Time hours after injection | Plasma GH ng/ml |
|---|---|---|---|
| Gly², Arg⁴, D-Tyr⁵, D-Trp⁸, D-Cys¹⁴-SRIF [des-Ala¹-Gly²], Arg⁴, D-Tyr⁵, D-Trp⁸, D-Cys¹⁴-SRIF | 1,000 | 6 | 114 ± 22 |

\* = p <0.01

Thus, [des-Ala$^1$-Gly$^2$], Arg$^4$, D-Tyr$^5$, D-Trp$^8$, D-Cys$^{14}$-Somatostatin, representative of the other compounds of the invention is an effective agent for reducing secretion of growth hormone, insulin, and glucagon and it exhibits very prolonged activity in suppressing growth hormone blood levels.

EXAMPLE 2

N$^α$-tert-butyloxycarbonyl-S-p-methoxybenzyl-L-cysteinyl-N$^{gn}$-tosyl-L-arginyl-N$^{gn}$-tosyl-D-arginyl-L-phenylalanyl-L-phenylalanyl-D-tryptophyl-ε-2-chlorobenzyloxycarbonyl-L-lysyl-0-benzyl-L-threonyl-L-phenylalanyl-0-benzyl-L-threonyl-0-benzyl-L-seryl-S-p-methoxybenzyl-L-cysteinyl-hydroxymethyl-polystyrene Chloromethylated polystyrene resin (Lab. Systems, Inc.) 1% cross-linked with divinylbenzene was esterified with Boc-Cys(SMBzl)-OH, according to Gisin, *Helv. Chim. Acta.*, 56, 1976 (1973). The polystyrene resin ester was treated according to Schedule A of Example 1 for the incorporation of Boc-Ser(Bzl)-OH, Boc-Thr(Bzl)-OH, Boc-Phe-OH, Boc-Thr(Bzl)-OH, Boc-Lys(CIZ)-OH, Boc-D-Trp-OH, Boc-Phe-OH, Boc-Phe-OH, Boc-D-Arg(Tos)-OH, Boc-Arg(Tos)-OH, and Boc-Cys(SMBzl)-OH, to afford the title peptidoresin.

L-Cysteinyl-L-arginyl-D-arginyl-L-phenylalanyl-L-phenylalanyl-D-tryptophyl-L-lysyl-L-threonyl-L-phenylalanyl-L-threonyl-L-seryl-L-cysteine cyclic (1→12)-disulfide tetraacetate (salt)

The peptido resin (10 g.) was mixed with anisole (15 ml.) and treated with 150 ml. liquid HF for 40 minutes at 10° C. The excess HF was evaporated under vacuo as fast as possible (ca. 45 minutes) and the residue was taken in 10% aqueous acetic acid and poured into 3,000 ml. of water. The ph was brought to 7 with dilute NH$_4$OH and then a solution of K$_3$Fe(CN)$_6$ (3 g. in 500 ml. water) was added dropwise until yellow. Ion exchange resin AG3-X4A (50 g.) was added and the suspension was filtered until no yellow color was present. The filtrate was passed through 70 g. of ion exchange resin Bio Rex-70 (cationic form) and the resin was washed with water, then the absorbed peptide was eluted with a mixture of pyridine-water-acetic acid, 30:4:60, v/v. The fractions containing the peptide were lyophilized to afford 1.8 g. of crude peptide. This crude peptide was chromatographed through a column of Sephadex G-15 (2.5×120 cm) and eluted with 10% aq. AcOH. Fractions of 5.5 ml. were collected and those which emerged in tubes 66 to 81 were pooled and lyophilized to yield the title compound, 500 mg.

$R_f$ (n-butanol-water-glacial acetic acid, 4:1:1, v/v) 0.56.

$R_f$ (n-butanol-water-glacial acetic acid-pyridine, 30:24:6:20:, v/v)0.69.

The product of Example 2 exhibits the following activity:

| Compd. | Dose μg/kg | GH ng/ml | INS μg/ml | GLUN pg/ml |
|---|---|---|---|---|
| Control | — | 141 ± 14 | 227 ± 19 | 61 ± 7 |
| Ex. 2 | 1,000 | 4 ± 3* | 89 ± 8* | 44 ± 8 |

The duration of activity was as follows:

| Compd. | Dose μg/kg | Hours | GH ng/ml |
|---|---|---|---|
| Control | — | 2 | 303 ± 53 |
| Ex. 2 | 1,000 | 2 | 54 ± 11** |
| Control | — | 4 | 73 ± 7 |
| Ex. 2 | 1,000 | 4 | 83 ± 9 |

*p <0.01
**p <0.001

EXAMPLE 3

L-Cysteinyl-L-arginyl-D-seryl-L-phenylalanyl-L-phenylalanyl-D-tryptophyl-L-lysyl-L-threonyl-L-phenylalanyl-L-threonyl-L-seryl-L-cysteine cyclic (1→12)-disulfide triacetate (salt)

The title dodecapeptide was prepared in a manner similar to the previous examples.

$R_f$ (n-butanol-water-glacial acetic acid, 4:1:1, v/v) 0.44.

$R_f$ (n-butanol-water-glacial acetic acid-pyridine, 15:12:3:10, v/v). 0.68.

Amino acid analysis: Thr(2) 1.68, L Ser(2) 1.57, Phe(3) 3, Lys(1) 0.96, Arg(1) 0.96, Cys(2) 1.54, Trp N.D.

The product of Example 3 exhibits the following activity:

| Compd. | Dose μg/kg | GH ng/ml | INS μU/ml | GLUN pg/ml |
|---|---|---|---|---|
| Control | — | 220 ± 17 | 34 ± 4 | 38 ± 6 |
| Ex. 3 | 2,000 | 37 ± 9* | 8 ± 1* | 26 ± 5 |

*p <0.01

The duration of activity was as follows:

| Compd. | Dose μg/kg | Hours | GH ng/ml | |
|---|---|---|---|---|
| Control | — | 2 | 290 ± 64 | |
| Ex. 3 | 1,000 | 2 | 91 ± 29 | p<0.02 |
| Control | — | 4 | 133 ± 38 | |
| Ex. 3 | 1,000 | 4 | 57 ± 12 | p<0.1 (not significant) |

EXAMPLE 4

L-Cysteinyl-L-arginyl-D-histidyl-L-phenylalanyl-L-phenylalanyl-D-tryptophyl-L-lysyl-L-threonyl-L-phenylalanyl-L-threonyl-L-seryl-L-cysteine cyclic (1→12) disulfide tetra-acetate (salt)

The title dodecapeptide was prepared in a manner similar to the previous examples.

$R_f$ (n-butanol-water-glacial acetic acid, 4:1:1, v/v) 0.52.

$R_f$ (n-butanol-water-glacial acid-pyridine, 15:12:3:10 v/v) 0.56.

The product of Example 4 exhibits the following activity:

| Compd. | Dose µg/kg | GH ng/ml | INS µU/ml | GLUN pg/ml |
|---|---|---|---|---|
| Control | — | 119 ± 29 | 280 ± 15 | 44 ± 6 |
| Ex. 4 | 500 | 6 ± 1* | 127 ± 22* | 29 ± 5 |

*p<0.01

The duration of activity was as follows:

| Compd. | Dose µg/kg | Hours | GH ng/ml | |
|---|---|---|---|---|
| Control | — | 2 | 82 ± 25 | |
| Ex. 4 | 1,000 | 2 | 24 ± 5 | p<0.05 |
| Control | — | 4 | 76 ± 28 | |
| Ex. 4 | 1,000 | 4 | 20 ± 7 | p<0.1 (not significant) |
| Control | — | 5 | 171 ± 38 | |
| Ex. 4 | 1,000 | 5 | 54 ± 11 | p<0.02 |
| Control | — | 6 | 73 ± 10 | |
| Ex. 4 | 1,000 | 6 | 54 ± 13 | |

EXAMPLE 5 tert-Butyloxycarbonyl-S-p-methoxybenzyl-L-cysteinyl-N$^\epsilon$-2-chlorobenzyloxycarbonyl-L-lysyl-0-2,6-dichlorobenzyl-D-tyrosyl-L-phenylalanyl-L-phenylalanyl-D-tryptophyl-N$^\epsilon$-2-chlorobenzyloxycarbonyl-L-lysyl-0-benzyl-L-threonyl-L-phenylalanyl-0-benzyl-L-threonyl-0-benzyl-L-seryl-S-p-methoxybenzyl-L-cysteinylhydroxymethyl polystyrene ester Chloromethylated polystyrene resin was esterified with Boc-Cys(SMBzl)-OH according to Gisin, *Helv. Chim. Acta*, 56, 1976 (1973) and the polymeric ester was treated according to Schedule A of Example 1 for the incorporation of Boc-Ser(Bzl)-OH, Boc-Thr(Bzl)-OH, Box-Phe-OH, Boc-Thr(Bzl)-OH, Boc-Lys(CIZ)-OH, Boc-D-Trp-OH, Boc-Phe-OH, Boc-Phe-OH, Boc-D-Tyr(Cl$_2$Bzl)-OH, Boc-Lys (CIZ)-OH, and Boc-Cys(SMBzl)-OH to afford the title peptidoresin.

L-Cysteinyl-L-lysyl-D-tyrosyl-L-phenylalanyl-L-phenylalanyl-D-tryptophyl-L-lysyl-L-threonyl-L-phenylalanyl-L-threonyl-L-seryl-L-cysteine cyclic (1→12) disulfide The peptido resin (9 g.) was suspended in anisole (18 ml.) and treated with liquid HF for 45 minutes after which time the excess HF was removed under vacuo and the residue extracted with 15% aq. AcOH. The mixture was filtered and the filtrate was washed with ether, then the aqueous layer was poured into 3.5 liters of water and the pH was brought to 7 with dil. NH$_4$OH. The linear reduced compound was oxidized with K$_3$Fe(CN)$_6$ and then the pH was brought to 5 with gl. AcOH. The excess oxidant was removed with Bio-Rad AG 3-X4A and the peptidic material absorbed on Bio-Rex 70. Elution with a mixture of pyridine-acetic acid-water, 30:4:66, v/v, afforded the crude material, 650 mg. This material was applied onto a column (2.5×84 cm.) of Sephadex G-15 and eluted with 15% aq. AcOH. The title dodecapeptide emerged in fractions 39 to 81 (4.7 ml. each fraction). 159.5 mg.

$R_f$(BWA, 4:1:1) 0.51, $R_f$(BWAP, 30:24:6:20) 0.65.
Amino acid analysis: Thr(2) 2.15 Ser(1) 1.01, Tyr(1) 0.89, Phe(3) 3 Lys(2) 2.13 Cys and Trp, not determined.

The duration of growth hormone suppression activity for the product of Example 5 was as follows:

| Compd. | Dose µg/kg | Hours | GH ng/ml |
|---|---|---|---|
| Control | — | 2 | 84 ± 17 |
| Ex. 5 | 1,000 | 2 | 27 ± 5* |
| Control | — | 2 | 141 ± 51 |
| Ex. 5 | 1,000 | 5 | 113 ± 27 |
| Control | — | 2 | 80 ± 12 |
| Ex. 5 | 1,000 | 2 | 72 ± 21 |
| Control | — | 4 | 84 ± 22 |
| Ex. 5 | 1,000 | 4 | 33 ± 4+ |

*p<0.01, +p<0.05

EXAMPLE 6 tert-Butyloxycarbonyl-S-p-methoxybenzyl-L-cysteinyl-N$^\epsilon$-2-chlorobenzyloxycarbonyl-L-lysyl-N$^{gn}$-tosyl-D-arginyl-L-phenylalanyl-L-phenylalanyl-D-tryptophyl-N$^\epsilon$-2-chlorobenzyloxycarbonyl-L-lysyl-0-benzyl-L-threonyl-L-phenylalanyl-0-benzyl-L-threonyl-0-benzyl-L-seryl-S-p-methoxybenzyl-L-cysteinyl-hydroxymethylpolystyrene ester.

The peptidoresin was prepared as in Example 1 and the same schedule A was applied for the incorporation of, Boc-Ser(Bzl)-OH, Boc-Thr(Bzl)-OH, Boc-Phe-OH, Boc-Thr(Bzl)-OH, Boc-Lys(CIZ)-OH, Boc-D-Trp-OH, Boc-Phe-OH, Boc-Phe-OH, Boc-D-Arg(Tos)-OH, Boc-Lys-(CIZ)-OH, and Boc-Cys(SMBzl)-OH.

L-Cysteinyl-L-lysyl-D-arginyl-L-phenylalanyl-L-Phenylalanyl-D-tryptophyl-L-lysyl-L-threonyl-L-phenylalanyl-L-threonyl-L-seryl-L-cysteine cyclic (1→12) disulfide The peptido resin (9 g.) of example 2 was treated with liquid HF in the presence of anisole and oxidized with K$_3$Fe(CN)$_6$ as in example 3 to afford 2.4 g. crude material. Part of this material was chromatographed through a column of Sephadex G15 and eluted with 15% Aq. AcOH. The material which emerged between fractions 67 and 93 was pooled and lyophilized (675) and then apssed through a partition column of Sephadex G-25 (n-butanol-water-gl. acetic acid, 4:5:1, v/v). The title compound emerged between fractions 78 to 100 (238 mg).

$R_f$(BWA, 4:1:1) 0.32, $R_f$(BWAP, 30:24:6:20) 0.62.
Amino acid analysis: Thr(2) 2.33, Ser(1) 1.13, Phe(3) 3, Lys(2) 2.23, Arg(1) 1.05, Cys and Trp not determined.

The product of Example 6 exhibits the following activity:

| Compd. | Dose µg/kg | GH ng/ml | INS µg/ml | GLUN pg/ml |
|---|---|---|---|---|
| Control | — | 220 ± 17 | 34 ± 4 | 38 ± 6 |
| Ex. 6 | 2,000 | 34 ± 8* | 5 ± 1* | 32 ± 5 |

The duration of activity was as follows:

| Compd. | Dose µg/kg | Hours | GH ng/ml |
|---|---|---|---|

| | | | |
|---|---|---|---|
| Control | — | 2 | 148 ± 25 |
| Ex. 6 | 1,000 | 2 | 53 ± 8* |
| Control | — | 4 | 73 ± 24 |
| Ex. 6 | 1,000 | 4 | 21 ± 4++ |

*$p<0.01$,
+$p<0.05$,
++$p<0.1$

The product of Examples 2–4 and 6 demonstrate highly selective inhibitory activity for growth hormone and insulin without meaningful effect on glucagon secretion. Thus, where preferential reduction of growth hormone and insulin are desired without change in glucagon levels, these compounds are of special interest.

The compounds described herein may be administered to warm blooded mammals, including humans, either intravenously, subcutaneously, intramuscularly, or orally to inhibit the release growth hormone and insulin where the host being treated requires therapeutic treatment for excess secretion of those substances as is frequently associated with conditions such as juvenile diabetes, hyperglycemia and acromegaly. The required dosage will vary with the particular condition being treated, the severity of the condition and the duration of treatment. If the active ingredient is administered in tablet form the tablet may contain: a binder such as gum tragacanth, corn starch, gelatin; and excipient such as dicalcium phosphate; a disintegrating agent such as corn starch, alginic acid, etc.; a lubricant such as magnesium stearate; and a sweetening and/or flavoring liquid. Carriers for intravenous administration include isotonic saline, phosphate buffer solutions, etc.

What is claimed is:

1. A polypeptide of the formula:

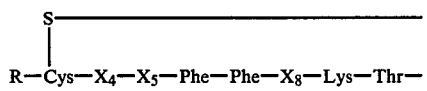
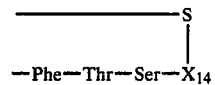

its linear precursors or a non-toxic acid addition salt thereof in which:

R is hydrogen, lower alkanoyl, benzoyl, Ala-Gly-, Gly-Gly-Gly, Ala-D-Ala, or p-Glu;
$X_4$ is Arg or Lys;
$X_5$ is D-Tyr, D-Trp, D-Ser, D-His or D-Arg;
$X_8$ is L-Trp or D-Trp and
$X_{14}$ is Cys or D-Cys.

2. The polypeptide of claim 1 which is L-cysteinyl-L-arginyl-D-tyrosyl-L-phenylalanyl-L-phenlalanyl-D-tryptophyl-L-lysyl-L-threonyl-L-phenylalanyl-L-threonyl-L-seryl-D-cysteine, the corresponding cyclic 1→12 disulfide or a non-toxic acid addition salt thereof.

3. The polypeptide of claim 1 which is L-cysteinyl-L-arginyl-D-seryl-L-phenylalanyl-L-phenylalanyl-D-tryptophyl-L-lysyl-L-threonyl-L-phenylalanyl-L-threonyl-L-seryl-L-cysteine, the corresponding cyclic 1→12 disulfide or a non-toxic acid addition salt thereof.

4. The polypeptide of claim 1 which is L-cysteinyl-L-arginyl-D-arginyl-L-phenylalanyl-L-phenylalanyl-D-tryptophyl-L-lysyl-L-threonyl-L-phenylalanyl-L-threonyl-L-seryl-L-cysteine, the corresponding cyclic 1→12 disulfide or a non-toxic acid addition salt thereof.

5. The polypeptide of claim 1 which is L-cysteinyl-L-arginyl-D-histidyl-L-phenylalanyl-L-phenylalanyl-D-tryptophyl-L-lysyl-L-threonyl-L-phenylalanyl-L-threonyl-L-seryl-L-cysteine, the corresponding cyclic 1→12 disulfide or a non-toxic acid addition salt thereof.

6. The polypeptide of claim 1 which is L-cysteinyl-L-lysyl-D-arginyl-L-phenylalanyl-L-phenylalanyl-D-tryptophyl-L-lysyl-L-threonyl-L-phenylalanyl-L-threonyl-L-seryl-L-cysteine, the corresponding cyclic 1→12 disulfide or a non-toxic acid addition salt thereof.

7. The polypeptide of claim 1 which is L-cysteinyl-L-lysyl-D-tyrosyl-L-phenylalanyl-L-phenylalanyl-D-tryptophyl-L-lysyl-L-threonyl-L-phenylalanyl-L-threonyl-L-seryl-L-cysteine, the corresponding cyclic 1→12 disulfide or a non-toxic acid addition salt thereof.

* * * * *